(12) United States Patent
Imagawa et al.

(10) Patent No.: US 9,875,539 B2
(45) Date of Patent: Jan. 23, 2018

(54) MEDICAL IMAGE PROCESSING APPARATUS AND MEDICAL IMAGE PROCESSING METHOD

(71) Applicant: Toshiba Medical Systems Corporation, Otawara-shi (JP)

(72) Inventors: Kazuo Imagawa, Nasushiobara (JP); Ryuji Zaiki, Utsunomiya (JP); Takayuki Ishikawa, Nasushiobara (JP); Masaki Kobayashi, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 15/257,664

(22) Filed: Sep. 6, 2016

(65) Prior Publication Data
US 2016/0371837 A1   Dec. 22, 2016

Related U.S. Application Data

(63) Continuation of application No. 14/455,047, filed on Aug. 8, 2014, now Pat. No. 9,462,986, which is a
(Continued)

(30) Foreign Application Priority Data

Mar. 2, 2012   (JP) ................................ 2012-046397

(51) Int. Cl.
  *G06K 9/00*   (2006.01)
  *G06T 7/00*   (2017.01)
  (Continued)

(52) U.S. Cl.
  CPC .............. *G06T 7/0012* (2013.01); *A61B 6/12* (2013.01); *A61B 6/463* (2013.01); *A61B 6/481* (2013.01);
  (Continued)

(58) Field of Classification Search
  None
  See application file for complete search history.

(56) References Cited

U.S. PATENT DOCUMENTS 8,090,177 B2 *  1/2012  Venkataraman ... A61B 1/00009
                                                  382/128
2004/0249270 A1  12/2004  Kondo et al.
(Continued)

FOREIGN PATENT DOCUMENTS

CN    103198202 A   7/2013
JP    2001-079097 A 3/2001
(Continued)

OTHER PUBLICATIONS

International Search Report dated May 14, 2013 for PCT/JP2013/055701 filed Mar. 1, 2013 with English Translation.
(Continued)

*Primary Examiner* — Weiwen Yang
(74) *Attorney, Agent, or Firm* — Oblon, McClelland, Maier & Neustadt, L.L.P.

(57) ABSTRACT

A medical image processing apparatus includes, an unit (12) extracting a blood vessel wall region from the image in a range including an aneurysm in an object, an unit (13) calculating the blood vessel diameter change rates of the neck portions of the aneurysm, blood vessel curvature, and blood vessel flattening ratio at each of discrete points on a blood vessel region based on the extracted blood vessel region, an unit (14) extracting, from discrete points, feature points at each of which at least one of a blood vessel diameter change rate, blood vessel curvature, and blood vessel flattening ratio exceeds a corresponding one of thresholds and decide a range for the indwelling of a stent graft in accordance with the extracted feature points, and a
(Continued)

display unit (19) superimposing and display unrecommended ranges on a stored image.

21 Claims, 10 Drawing Sheets

Related U.S. Application Data continuation of application No. PCT/JP2013/055701, filed on Mar. 1, 2013.

(51) Int. Cl.
  *A61B 6/12* (2006.01)
  *A61F 2/82* (2013.01)
  *G06K 9/46* (2006.01)
  *G06T 7/11* (2017.01)
  *G06T 7/62* (2017.01)
  *G06T 7/64* (2017.01)
  *A61B 6/00* (2006.01)

(52) U.S. Cl.
  CPC .............. *A61B 6/487* (2013.01); *A61B 6/504* (2013.01); *A61B 6/5217* (2013.01); *A61F 2/82* (2013.01); *G06K 9/4604* (2013.01); *G06T 7/11* (2017.01); *G06T 7/62* (2017.01); *G06T 7/64* (2017.01); *A61B 6/501* (2013.01); *A61F 2002/823* (2013.01); *G06T 2207/10081* (2013.01); *G06T 2207/30101* (2013.01)

(56) References Cited

U.S. PATENT DOCUMENTS

| | | |
|---|---|---|
| 2005/0010100 A1 | 1/2005 | Hornegger et al. |
| 2006/0280351 A1 | 12/2006 | Luping |
| 2009/0018562 A1* | 1/2009 | Amplatz ............ A61B 17/0057 606/157 |
| 2010/0286791 A1 | 11/2010 | Goldsmith |
| 2010/0309198 A1 | 12/2010 | Kauffmann |
| 2012/0150048 A1 | 6/2012 | Kang |

FOREIGN PATENT DOCUMENTS

| | | |
|---|---|---|
| JP | 2002-233579 A | 8/2002 |
| JP | 2003-245360 A | 9/2003 |
| JP | 2004-201873 A | 7/2004 |
| JP | 2004-283373 A | 10/2004 |
| JP | 2004-329929 A | 11/2004 |
| JP | 2005-198708 A | 7/2005 |
| JP | 2006-048247 A | 2/2006 |
| JP | 2010-088795 A | 4/2010 |
| JP | 2011-045449 A | 3/2011 |

OTHER PUBLICATIONS

International Written Opinion dated May 14, 2013 for PCT/JP2013/055701 filed Mar. 1, 2013.
Takuya Kusu, et al. "Improved of the method for detecting aneurysms based on measurement of cerebral vascular diameter from MR Angiogram", IEICE Technical Report, MI, Iyo Gazo, 2007, vol. 107, No. 326, p. 49-54 with English Translation.
Wataru Higashiura, et al. "Impact of 3-dimensional-computed tomography workstation for precise planning of endovascular aneurysm repair", Circulation journal: official journal of the Japanese Circulation Society, 2008, vol. 72, No. 12, p. 2028-2034.
David R. Whittaker, et al. "Prediction of altered endograft path during endovascular abdominal aortic aneurysm repair with the Gore Excluder", The New England Society for Vascular Surgery, 2005, vol. 41, No. 4, p. 575-583.
Wataru Higashiura, "Daidomyaku Shikkan ni Taisuru Stent Graft Chiryo", Shiyaku to Shin'yaku, 07, 2009, vol. 46, No. 7, p. 678-679.
Naoto Hayashi, et al. "Feasibility of a curvature-based enhanced display system for detecting cerebral aneurysms in MR Angiography", Magnetic Resonance in Medical Sciences, 2003, vol. 2, No. 1, p. 29-36.
Elliot L. Chaikof, et al. "Identifying and grading factors that modify the outcome of endovascular aortic aneurysm repair", Journal of Vascular Surgery, 2002, vol. 35, No. 5, p. 1061-1066.
Combined Office Action and Search Report dated Feb. 27, 2015 in Chinese Patent Application No. 201380000221.2 (with English translation of categories of cited documents).
International Preliminary Report on Patentability and Written Opinion dated Sep. 12, 2014, in International application No. PCT/JP2013/055701 (English translation only).

* cited by examiner

FIG. 7 — Aneurysm is specified from morphological features of aneurysm (pattern recognition processing and like)

FIG. 8 — Flattening ratio and curvature are calculated at each of multiple points on blood vessel wall other than aneurysm and diameter change rate is calculated in range of each point and its adjacent points (blood vessel diameter is distance between blood vessel walls in direction perpendicular to blood vessel centerline)

Point at which at least one of diameter change rate, flattening ratio, and curvature exceeds corresponding one of thresholds is extracted

FIG. 9

Boundary line of unrecommended range perpendicular to blood vessel centerline

Unrecommended range is specified in accordance with extracted point strings

MEDICAL IMAGE PROCESSING APPARATUS AND MEDICAL IMAGE PROCESSING METHOD

CROSS-REFERENCE TO RELATED APPLICATIONS

This application is a continuation application of, and claims the benefit of priority under 35 U.S.C. §120 from, U.S. application Ser. No. 14/455,047, filed Aug. 8, 2014, which is a continuation application of PCT Application No. PCT/JP2013/055701, filed Mar. 1, 2013, which claims the benefit of priority under 35 U.S.C. §119 from Japanese Patent Application No. 2012-046397, filed Mar. 2, 2012, the entire contents of all of which are incorporated herein by reference.

FIELD

Embodiments described herein relate generally to a medical image processing apparatus and a medical image processing method.

BACKGROUND

Stent grafting is a medical treatment for preventing the rupture of an aortic aneurysm by indwelling an artificial blood vessel (graft) embedded with a mesh metal tube (stent) in the aortic aneurysm and blocking the inflow of blood into the aneurysm. In general, when executing a treatment plan, an operator performs image examination first by using an x-ray computer tomography apparatus (CT), and then selects a stent graft suitable for the blood vessel shape from the resultant image. The operator then indwells the stent graft under x-ray fluoroscopy.

A challenge of stent grafting is to suppress endoleak which sometimes occurs after the indwelling of a stent graft. Endoleak is a phenomenon in which blood leaks from the gap between an end portion of a stent graft and the inner wall of a blood vessel. In order to eliminate such a gap, it is required to carefully decide stent graft indwelling positions.

CITATION LIST

Patent Literature

Patent Literature 1: Jpn. Pat. Appln. KOKAI Publication No. 2010-088795

It is an object to provide information for supporting the decision of stent graft indwelling positions.

DETAILED DESCRIPTION

A medical image processing apparatus according to this embodiment will be described below with reference to the accompanying drawings. The medical image processing apparatus according to the embodiment includes an image storage unit which stores the data of a processing target image. The processing target image includes the aneurysm in an object and a blood vessel portion in which the aneurysm is formed. This apparatus extracts a blood vessel wall region from the image. The apparatus calculates a blood vessel diameter change rate, blood vessel curvature, and blood vessel flattening ratio at each of a plurality of discrete points on the blood vessel wall region from the extracted blood vessel wall region. The apparatus extracts feature points, from the plurality of discrete points, at each of which at least one of the blood vessel diameter change rate, blood vessel curvature, and blood vessel flattening ratio exceeds a corresponding one of thresholds. The apparatus decides a range for the indwelling of a stent graft for the aneurysm in accordance with the extracted feature points. Each decided range is superimposed and displayed on an image.

The terms used will be defined first as follows.

Figure 18:
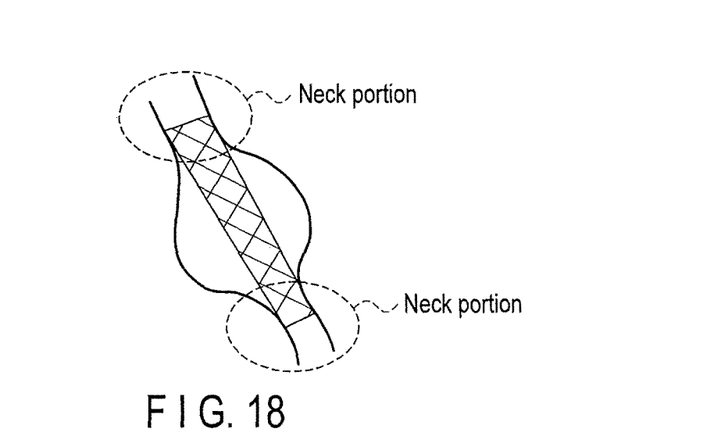
FIG. 18 is a view showing the neck portions of an aneurysm.
Figure 19:
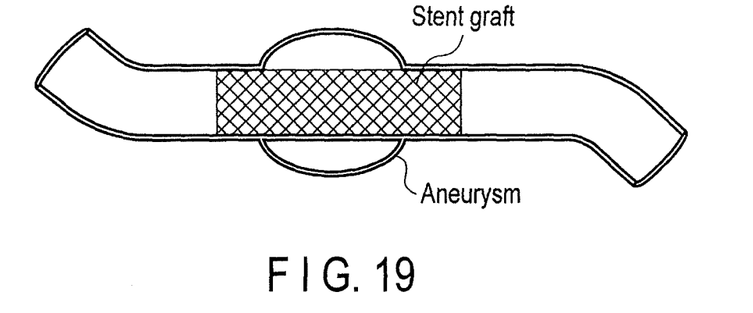
FIG. 19 is a view showing a stent graft indwelled in the neck portions of an aneurysm.

As shown in FIG. 18, neck portions are healthy blood vessel portions, of a blood vessel with an aneurysm, which lead to the aneurysm from its two sides. In practice, the neck portions are blood vessel portions in an ROI (to be described later) and located in ranges excluding the aneurysm region. As shown in FIG. 19, it is possible to properly suppress endoleak by bringing the outer circumferential portions of the two ends of a stent graft into tight contact with the inner walls of the neck portions. This suppression can suppress a local abnormal dilation of a blood vessel, i.e., an aneurysm.

Unrecommended regions are blood vessel portions, of neck portions, which are not suitable for the indwelling of a stent graft, i.e., blood vessel portions with high possibility of endoleak. Note that this embodiment has a feature that it technically defines blood vessel portions unsuitable for the indwelling of a stent graft, automatically identifies such unrecommended regions in accordance with the definition, and presents the unrecommended regions to an operator (doctor) to support making a treatment plan.

Recommended regions are blood vessel portions suitable for the indwelling of a stent graft, i.e., blood vessel portions with low possibility of endoleak. For example, recommended regions are blood vessel portions obtained by excluding unrecommended regions from neck portions. Such regions will be described in detail later.

Endoleak is a phenomenon that gaps are formed between the outer circumferential portions of the two ends of a stent graft and the inner wall portions of a blood vessel at neck portions after the indwelling of the stent graft to make blood leak from the gaps, thereby causing suppressed blood to flow into the aneurysm. Gaps are formed mainly due to insufficient contact between the outer circumferential portions of the two ends of a stent graft and the inner wall portions of a blood vessel at neck portions.

An ROI (Region of Interest) is originally a region of user's interest. In this case, an ROI is particularly a local range which forms an inner portion of an image set by the user as a processing target range for the identification of unrecommended regions and recommended regions.

Figure 1:
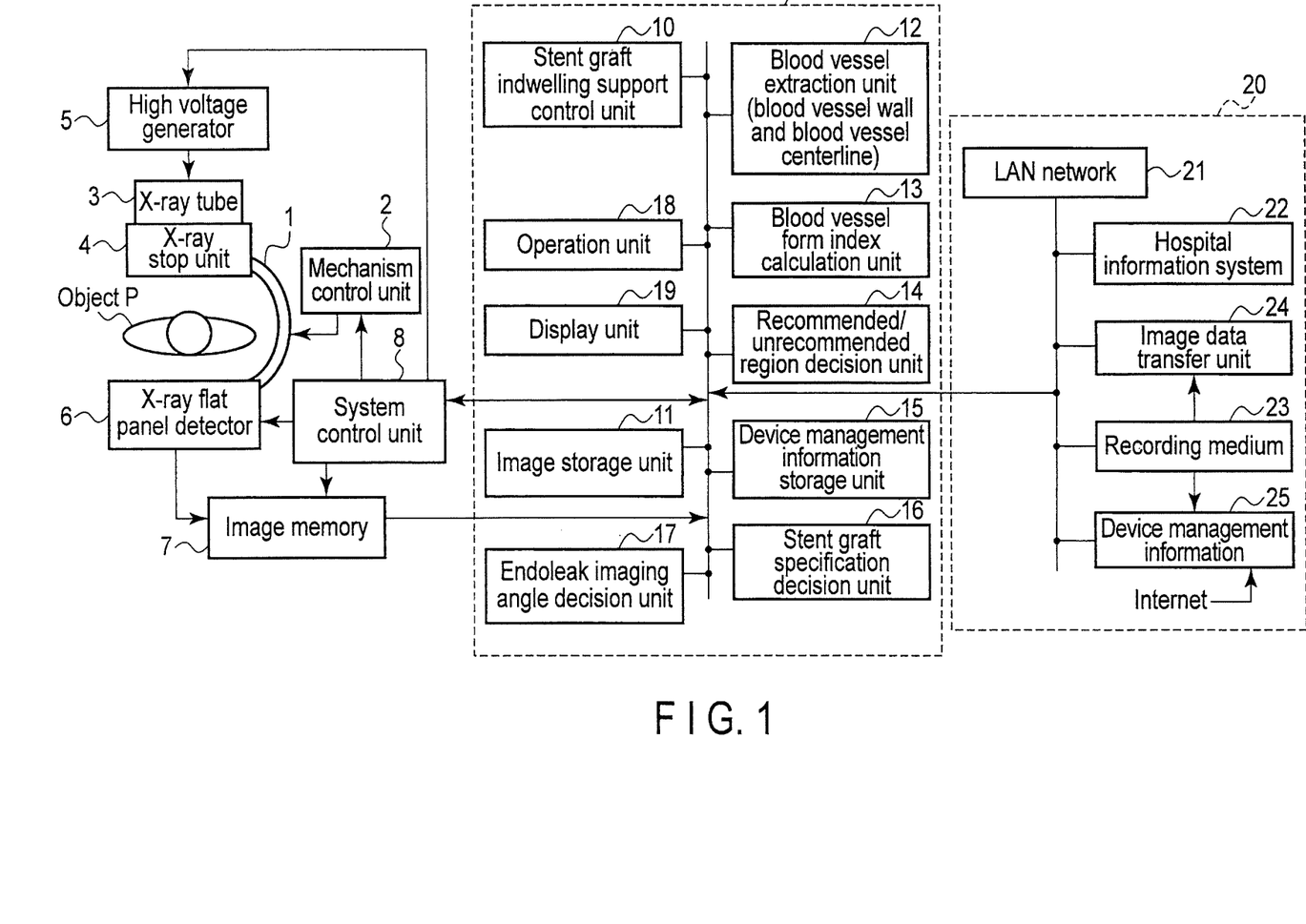
FIG. 1 is a block diagram showing the arrangement of an X-ray angiographic diagnostic apparatus including a stent graft indwelling support apparatus according to an embodiment.

FIG. 1 is a block diagram showing the arrangement of an X-ray angiographic diagnostic apparatus including a stent graft indwelling support apparatus according to this embodiment. An X-ray tube 3 generates X-rays upon receiving a high voltage (tube voltage) and a filament current from a high voltage generator 5. An X-ray stop unit 4 for forming X-rays in an arbitrary shape is attached to the X-ray emission window of the X-ray tube 3. The X-ray tube 3 is attached to one end of an arm 1 in the shape of, for example, C. An X-ray flat panel detector 6 facing the X-ray tube 3 is attached to the other end of the C-arm 1. The X-ray flat panel detector 6 is a so-called flat panel detector, which has a plurality of detection elements arrayed two-dimensionally to directly or indirectly convert incident X-rays into electric charge. An output from the X-ray flat panel detector 6 is supplied as X-ray image data to a stent graft indwelling support apparatus 9 via an image memory 7. An object P placed on a bed (not shown) is disposed between the X-ray tube 3 and the X-ray flat panel detector 6. A support mechanism (not shown) supports the C-arm 1 so as to allow it to independently rotate about three orthogonal axes. A mechanism control unit 2 controls the support mechanism of the C-arm 1 to arbitrarily change an imaging angle (working angle) relative to the object P. When performing imaging, a system control unit 8 controls the mechanism control unit 2, the high voltage generator 5, the X-ray flat panel detector 6, and the image memory 7.

The stent graft indwelling support apparatus 9 includes a stent graft indwelling support control unit 10 as a main unit and an image storage unit 11. The image storage unit 11 stores image data in a range including the aneurysm, which is generated by a medical image generation apparatus such as an X-ray computed tomography apparatus (CT) for the object. This image data is typically a tomographic image, which will be described as a CT image. The operator sets, as a processing target, a local range (a region of interest ROI in this case) including an aneurysm on a CT image via an operation unit 18.

A blood vessel extraction unit 12 extracts a blood vessel wall region by arbitrary processing such as threshold processing upon localization to the region of interest ROI of the tomographic image, and also specifies a blood vessel centerline from the extracted blood vessel wall region. A blood vessel centerline is specified as a string of points equidistant from, typically, the inner blood vessel wall on one side and the inner blood vessel wall on the opposite other side on the tomographic image. The blood vessel extraction unit 12 extracts a plaque portion and a calcified portion by localization to the region of interest ROI on the tomographic image by threshold processing using thresholds unique to the plaque portion and the calcified portion.

A blood vessel form index calculation unit 13 calculates indices (blood vessel form indices) representing a blood vessel form concerning the neck portions of the aneurysm based on the extracted blood vessel region and blood vessel centerline. The blood vessel form index calculation unit 13 calculates, as blood vessel form indices, a blood vessel diameter change rate, blood vessel curvature, and blood vessel flattening ratio at each of a plurality of discrete points which are located on the blood vessel centerline and arranged at equal intervals. A blood vessel diameter is the distance between the intersections of a line orthogonal to a blood vessel centerline at each discrete point and the inner wall portions of a blood vessel wall region on the two sides. A blood vessel diameter change rate is calculated as the value obtained by normalizing the difference between the maximum blood vessel diameter and the minimum blood vessel diameter in a predetermined range centered on each point on the blood vessel centerline with the blood vessel diameter at the corresponding point. A blood vessel curvature is the curvature of a blood vessel centerline at each of a plurality of points on a blood vessel centerline. A blood vessel flattening ratio is the ratio of the minimum blood vessel diameter to the maximum blood vessel diameter on a blood vessel cross-section orthogonal to a blood vessel centerline at each of the plurality of points on the blood vessel centerline. Note that an MPR processing unit (not shown) may generate a tomographic image of a blood vessel cross-section from volume data in a range including the aneurysm by MPR (Multi Planar Reconstruction). Alternatively, the tomographic image data of a blood vessel cross-section may be received from an external system 20.

A recommended/unrecommended region decision unit 14 extracts, from a plurality of discrete points on a blood vessel centerline, points at which the blood vessel diameter change rates exceed the first threshold. The recommended/unrecommended region decision unit 14 extracts, from the plurality of discrete points on the blood vessel centerline, points at which the blood vessel curvatures exceed the second threshold. The recommended/unrecommended region decision unit 14 also extracts, from the plurality of discrete points on the blood vessel centerline, points at which the blood vessel flattening ratios exceed the third threshold. In addition, the recommended/unrecommended region decision unit 14 extracts, as a plurality of unrecommended points (feature points), a plurality of points at each of which at least one of the blood vessel diameter change rate, blood vessel curvature, and blood vessel flattening ratio exceeds a corresponding one of thresholds. Furthermore, the recommended/unrecommended region decision unit 14 extracts, as unrecommended points, points included in circles each having, as its radius, a predetermined distance from an end portion of each of the extracted plaque and calcified portions.

The recommended/unrecommended region decision unit 14 decides an unrecommended region from a range in which a plurality of extracted unrecommended points constitute strings. Note that the recommended/unrecommended region decision unit 14 may decide a single unrecommended region or a plurality of discrete unrecommended regions.

The recommended/unrecommended region decision unit 14 decides recommended regions. The recommended regions are those obtained by excluding the unrecommended regions from the neck portions. The recommended/unrecommended region decision unit 14 decides, as a recommended region, a region having both a blood vessel diameter change rate and a curvature which are less than the corresponding thresholds or other lower thresholds and a length exceeding the necessary length of an end portion of the stent graft.

A display unit 19 superimposes and displays translucent area marks respectively indicating the recommended regions and the unrecommended regions on a tomographic image of a blood vessel cross-section under the control of the stent graft indwelling support control unit 10. An area mark indicating an unrecommended region has a display form, e.g., a color, different from that of an area mark indicating a recommended region. The operator designates stent graft indwelling planned positions in the respective recommended regions of the neck portions on the two sides of the aneurysm while checking the recommended regions and the unrecommended regions on the image. In this case, the stent graft indwelling planned positions are the positions of one end portion and the other end portion of the stent graft.

A stent graft specification decision unit 16 decides specifications concerning a stent graft required for this aneurysm treatment based on the stent graft indwelling planned positions and the blood vessel form indices. In general, the specifications of a stent graft are often given by an aneurysm size, neck diameters, and maximum curvature. The stent graft specification decision unit 16 decides an "aneurysm size" from the distance between the indwelling planned positions on the two sides. The stent graft specification decision unit 16 decides "neck diameters" from blood vessel diameters at the indwelling planned positions on the two sides. The stent graft specification decision unit 16 decides the maximum value of the blood vessel curvatures between the indwelling planned positions on the two sides as a "maximum curvature".

The stent graft specification decision unit 16 searches an information database concerning many stent graft products, which is stored in advance in a device management information storage unit 15, according to the decided stent graft specifications, and extracts at least one stent graft product having specifications matching the stent graft specifications.

An endoleak imaging angle decision unit 17 decides, at the stent graft indwelling planned positions, a position, in the contact ranges between the two ends of the stent graft and the blood vessel wall, at which the possibility of the occurrence of endoleak is highest, and an imaging angle which most facilitates visual recognition of the occurrence of endoleak at the decided position. More specifically, the endoleak imaging angle decision unit 17 specifies a point, in the contact ranges between the two ends of the stent graft and the blood vessel wall, at which the blood vessel flattening ratio is highest. The endoleak imaging angle decision unit 17 decides this point as the center of an imaging field of view. The endoleak imaging angle decision unit 17 also decides, as an imaging angle, a direction orthogonal to a plane determined by the longest diameter passing through the point at which the the blood vessel flattening ratio is highest and a blood vessel centerline segment intersecting the diameter at the point and located near the point.

The display unit 19 superimposes and displays area marks indicating unrecommended regions and recommended regions on the CT image data stored in the image storage unit 11 or the live image generated by the X-ray angiographic diagnostic apparatus incorporated in the stent graft indwelling support apparatus 9. A concrete example of the display form of area marks will be described later. At the stage of planning a stent graft indwelling planned treatment, the doctor can decide stent graft indwelling planned positions by visually checking unrecommended regions and recommended regions and the forms of an aneurysm and blood vessel portions near it on a CT image. In addition, at the stage of operating during a stent graft indwelling treatment, the doctor can execute the operation of indwelling the stent graft while visually checking the unrecommended regions and recommended regions on a live image.

The stent graft indwelling support apparatus 9 may generate stent graft indwelling support information from a medical imaging apparatus other than the X-ray angiographic diagnostic apparatus incorporated in the stent graft indwelling support apparatus 9 or from past image data concerning the object which is stored in an external system. With regard to past image data, the stent graft indwelling support apparatus 9 may generate stent graft indwelling support information from, for example, the image data which can be supplied from a hospital information system 22 of the external system 20 via a LAN network 21 in the hospital or from the image data supplied from a recording medium 23 such as a memory card via an image data transfer unit 24. Images to be used may be X-ray images, CT images, MRI images, and images generated by other modalities.

The device management information storage unit 15 stores device management information concerning various types of stent graft products which is supplied via the Internet or the recording medium 23. Device management information includes information concerning specifications such as the model numbers, shapes, and sizes of various stent graft products (called devices) provided from a plurality of stent graft providers. The stent graft specification decision unit 16 decides specifications concerning the thickness, curvature, and length required for a stent graft in accordance with the blood vessel diameters at the two end portions of the stent graft at indwelling planned positions, the maximum curvature of the two end portions, and the length between the two end portions, which are set in accordance with operator instructions input via the operation unit 18, and extracts device management information from devices (stent graft products) satisfying the specifications. The display unit 19 displays a list of such products.

Figure 2:
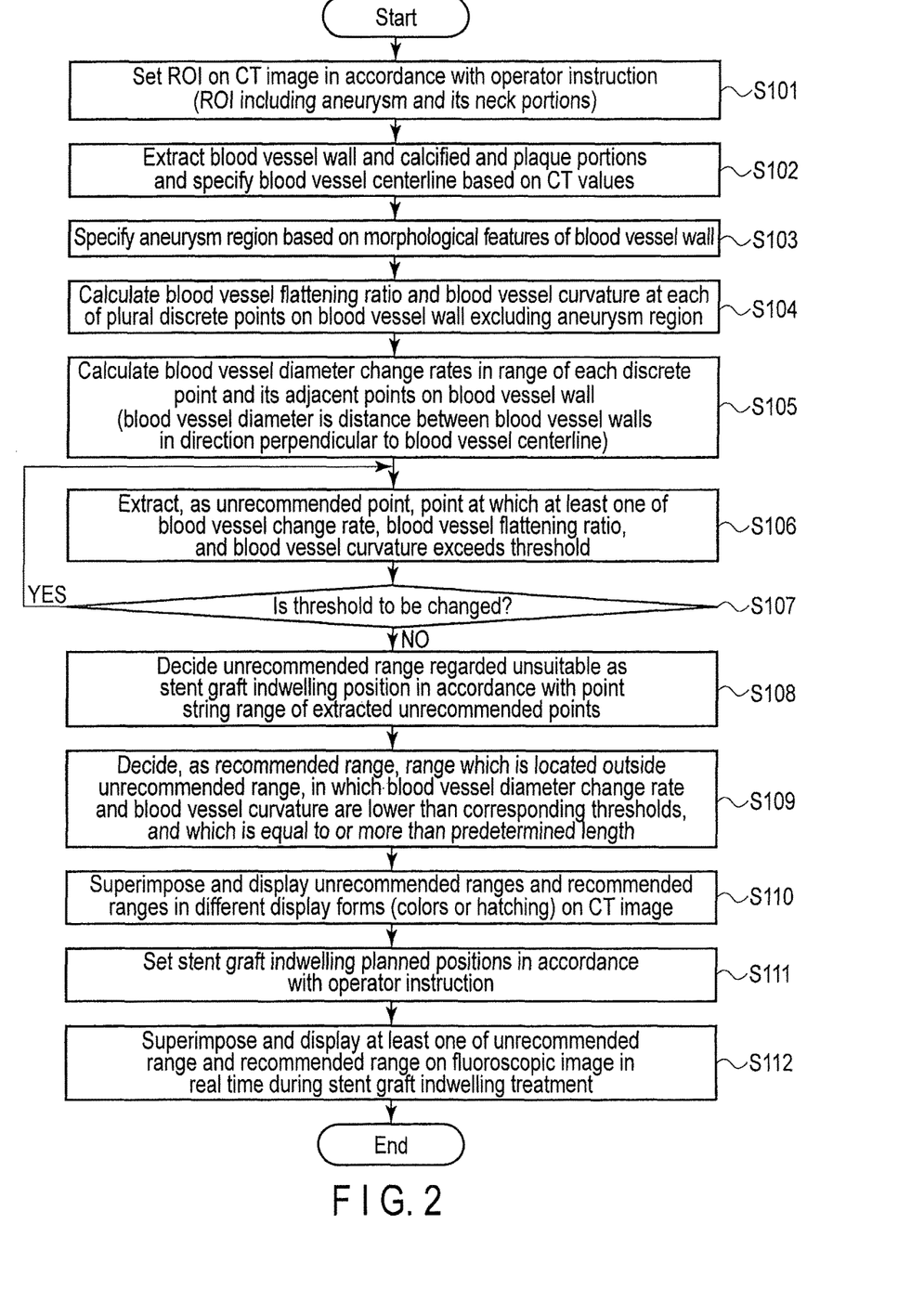
FIG. 2 is a flowchart showing a procedure for decision support processing for stent graft indwelling planned positions by the stent graft indwelling support apparatus in FIG. 1.

FIG. 2 shows a procedure for decision support processing for stent graft indwelling planned positions in this embodiment. The final object of this support processing is to superimpose and display area marks indicating recommended regions recommended as stent graft indwelling positions and area marks indicating unrecommended regions unrecommended as stent graft indwelling positions on a tomographic image, and provide device information of a stent graft product corresponding to stent graft indwelling planned positions. This processing provides an imaging angle suitable for a check on the occurrence of endoleak after operation.

Figure 5:
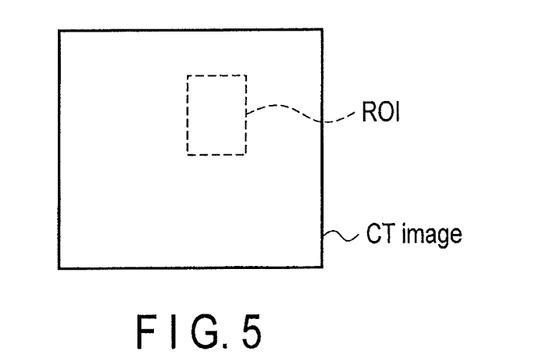
FIG. 5 is a view corresponding to step S101 in FIG. 2.
Figure 6:
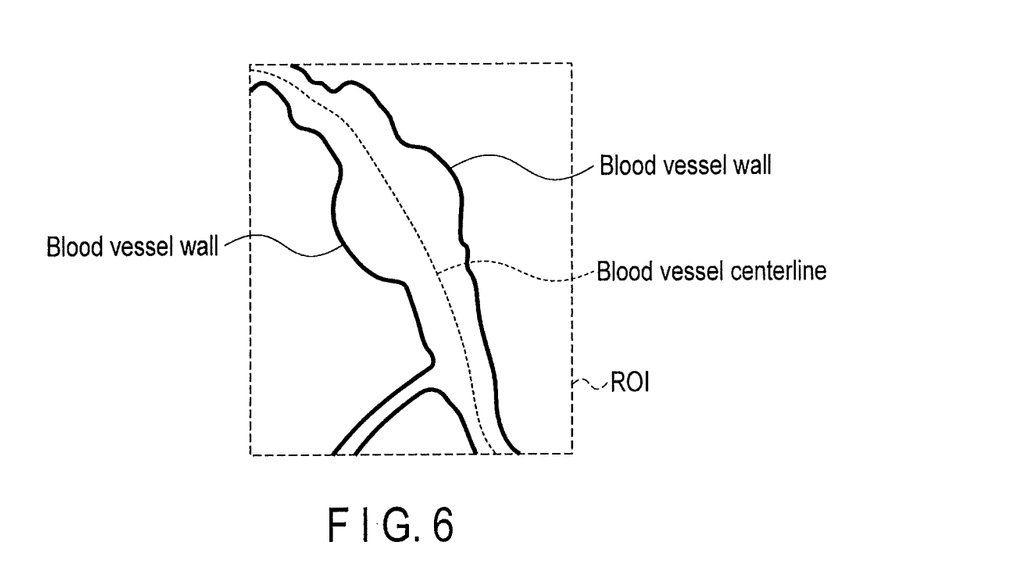
FIG. 6 is a view corresponding to step S102 in FIG. 2.
Figure 7:
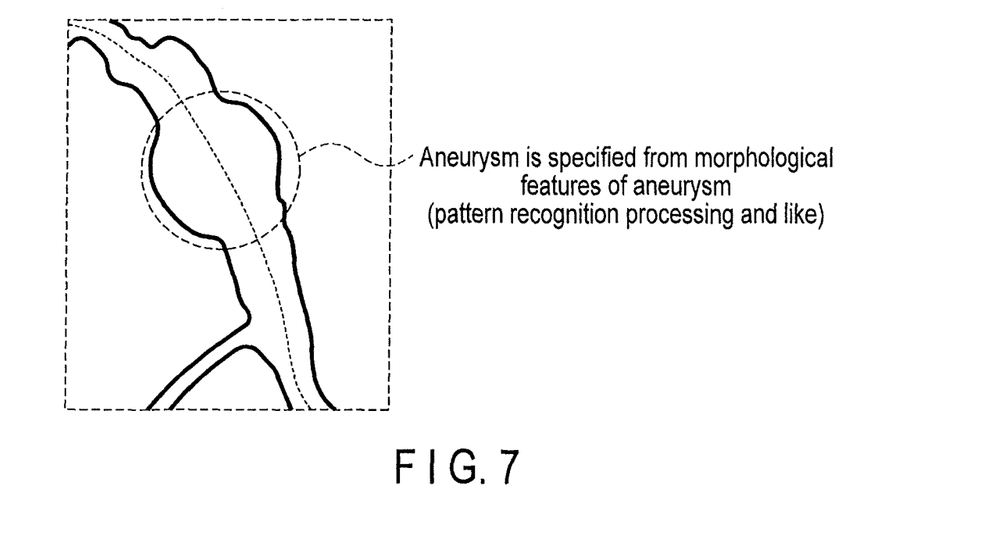
FIG. 7 is a view corresponding to step S103 in FIG. 2.

As shown in FIG. 5, the operator operates the operation unit 18 to set a region of interest ROT on a portion of a CT image of a longitudinal section of the target blood vessel displayed on the display unit 19 (step S101). A decision support processing target for stent graft indwelling planned positions is limited to the region of interest ROI. In step S102, the blood vessel extraction unit 12 extracts a blood vessel region by localization to the region of interest ROI of the tomographic image by threshold processing, as shown in FIG. 6. The blood vessel extraction unit 12 specifies a blood vessel centerline as a string of points equidistant from opposite blood vessel wall regions. The blood vessel extraction unit 12 extracts a plaque portion and a calcified portion by threshold processing using thresholds unique to the plaque portion and the calcified portion upon localization to the region of interest ROI of the tomographic image. In step S103, the blood vessel extraction unit 12 specifies an aneurysm region by, for example, pattern recognition for an extracted blood vessel wall region (FIG. 7).

Figure 8:
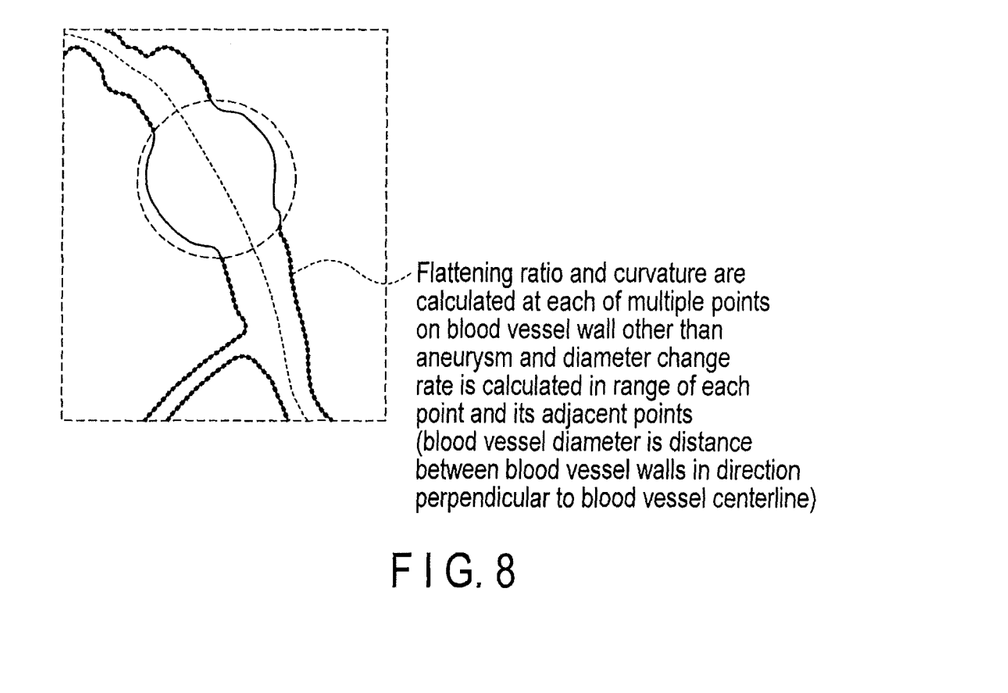
FIG. 8 is a view showing discrete points corresponding to step S104 in FIG. 2.

As shown in FIG. 8, based on an extracted blood vessel wall region and blood vessel centerline, the blood vessel form index calculation unit 13 calculates a blood vessel diameter change rate, blood vessel curvature, and blood vessel flattening ratio at each of multiple discrete points on a blood vessel wall region other than the aneurysm region or the blood vessel centerline (step S105). As described above, the blood vessel form index calculation unit 13 calculates, as a blood vessel diameter, the distance between the intersections of a line orthogonal to a blood vessel centerline at each discrete point and the inner wall portions of a blood vessel wall region on the two sides. The blood vessel form index calculation unit 13 calculates, as a blood vessel diameter change rate, the value obtained by normalizing the difference between the maximum blood vessel diameter and the minimum blood vessel diameter in a predetermined range centered on each point on a blood vessel centerline with the blood vessel diameter at the point. The blood vessel form index calculation unit 13 calculates, as a blood vessel curvature, the curvature of a blood vessel centerline at each of a plurality of points on the blood vessel centerline. The blood vessel form index calculation unit 13 calculates, as a blood vessel flattening ratio, the ratio of the minimum blood vessel diameter to the maximum blood vessel diameter on a blood vessel cross-section orthogonal to a blood vessel centerline at each of a plurality of points on the blood vessel centerline.

Figure 9:
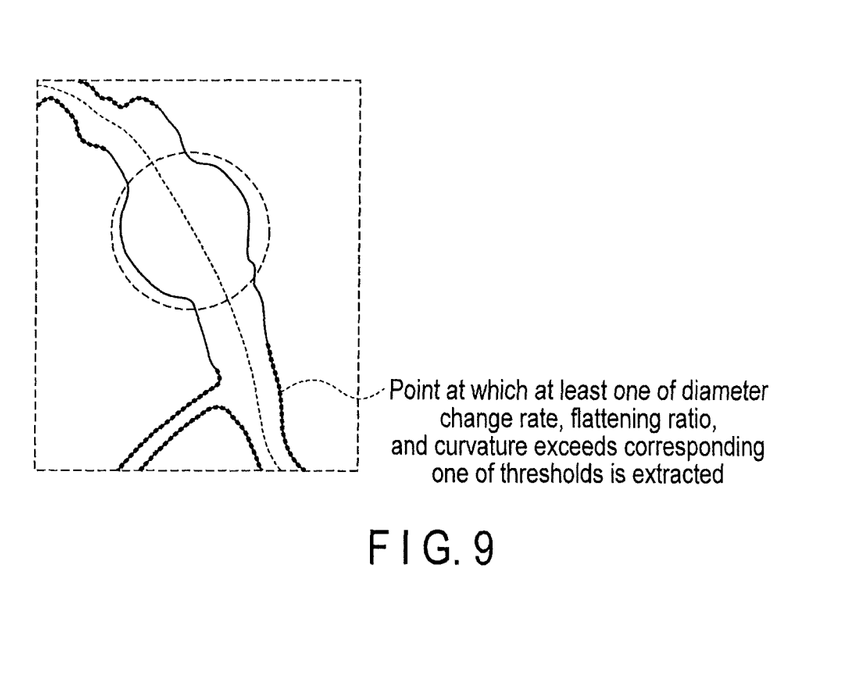
FIG. 9 is a view corresponding to step S104 in FIG. 2.

The recommended/unrecommended region decision unit 14 decides regions (recommended regions) recommended as stent graft indwelling positions and regions (unrecommended regions) which are not recommended, based on these calculated blood vessel form indices (step S106). More specifically, as shown in FIG. 9, the recommended/unrecommended region decision unit 14 extracts, as unrecommended points, points, from a plurality of discrete points on a blood vessel centerline, at each of which at least one of the blood vessel diameter change rate, blood vessel curvature, and blood vessel flattening ratio exceeds a corresponding one of thresholds determined for the respective values. In addition, the recommended/unrecommended region decision unit 14 extracts, as unrecommended points, points included in circles each having, as its radius, a predetermined distance from an end portion of each of the extracted plaque and calcified portions. Note that the operator can arbitrarily change the thresholds respectively determined for blood vessel diameter change rates, blood vessel curvatures, and blood vessel flattening ratios (step S107).

The recommended/unrecommended region decision unit 14 decides one or two or more unrecommended regions in accordance with the point string range of the extracted unrecommended points (step S108). The recommended/unrecommended region decision unit 14 also decides, as a recommended region, a region which is obtained by excluding an unrecommended region from a neck portion. This region corresponds to a point string range of discrete points in which both a blood vessel diameter change rate and a curvature are less than the corresponding thresholds or other lower thresholds. The region also has a length exceeding the necessary length of an end portion of the stent graft (step S109).

Figure 10:
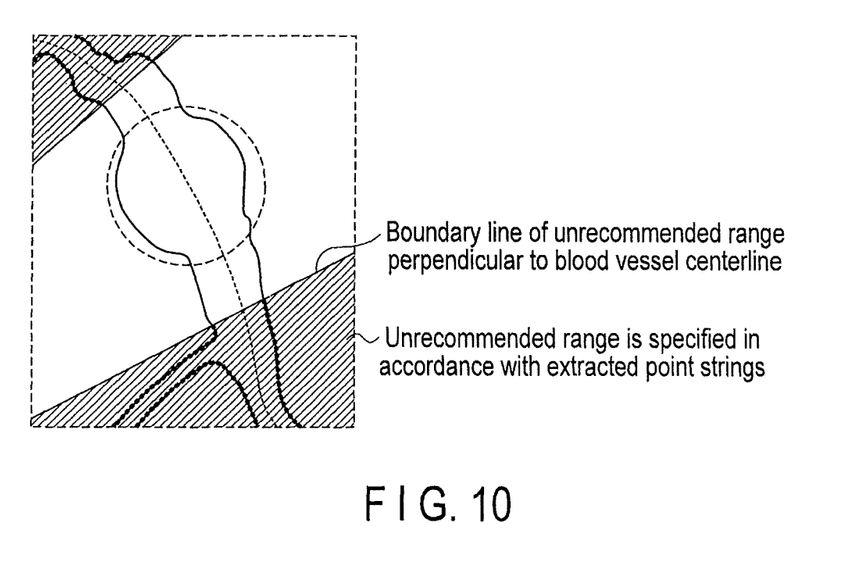
FIG. 10 is a view corresponding to steps S105 to S108 in FIG. 2.
Figure 11:
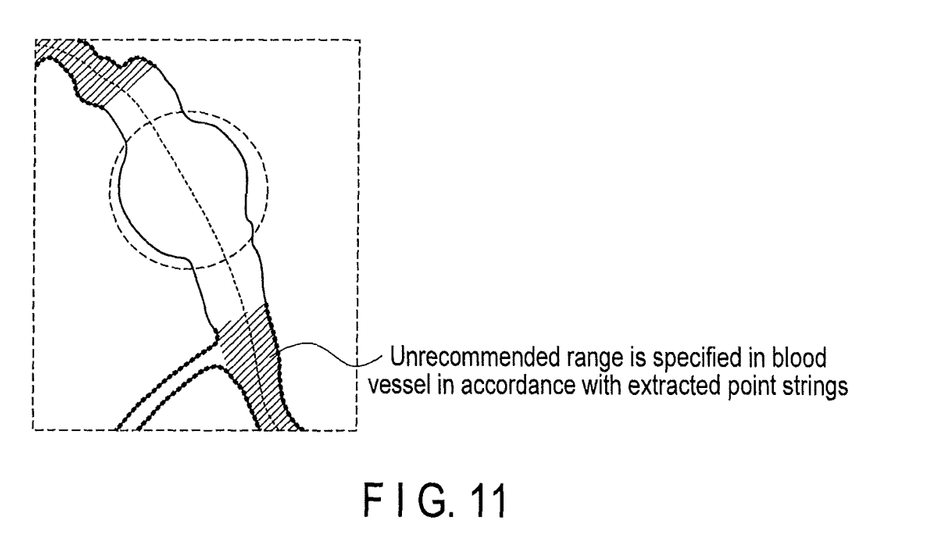
FIG. 11 is a view corresponding to step S109 in FIG. 2.
Figure 12:
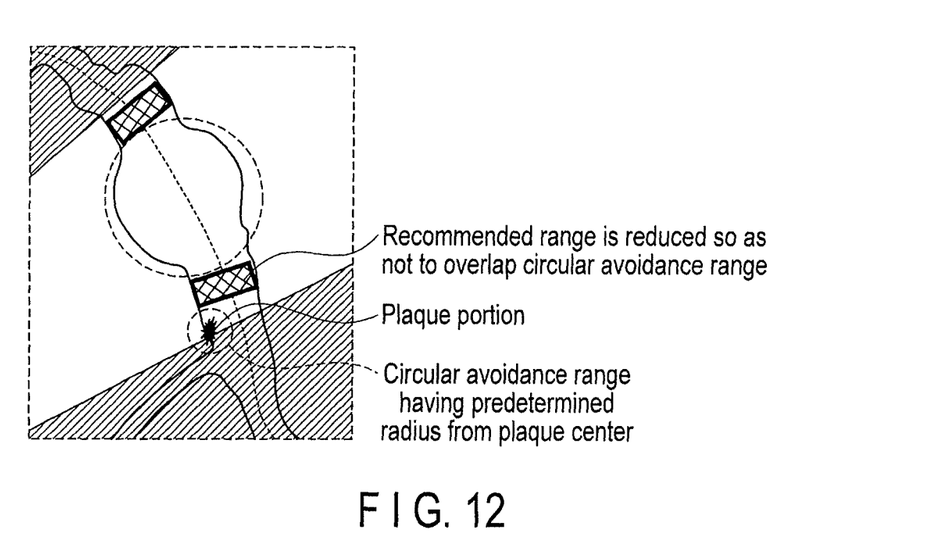
FIG. 12 is a view corresponding to step S109 in FIG. 2.

As shown in FIGS. 10, 11, and 12, the display unit 19 superimposes and displays translucent area marks indicating the unrecommended regions on a tomographic image of a blood vessel cross-section under the control of the stent graft indwelling support control unit 10 (step S110). The display unit 19 displays area marks indicating recommended regions together with the area marks indicating the unrecommended regions, as needed. In this case, the display unit 19 displays the area marks indicating the unrecommended regions in a display form, typically, a color, different from that of the area marks indicating the recommended regions. The operator operates the operation unit 18 to designate stent graft indwelling planned positions in the respective recommended regions of the neck portions on the two sides of the aneurysm while checking the recommended regions and the unrecommended regions on the image (step S111). In practice, when the doctor performs stent graft indwelling treatment under X-ray fluoroscopy, area marks indicating unrecommended regions are superimposed on a real-time fluoroscopic image. Area marks indicating recommended regions are also superimposed on the real-time fluoroscopic image, as needed (step S112).

Figure 3:
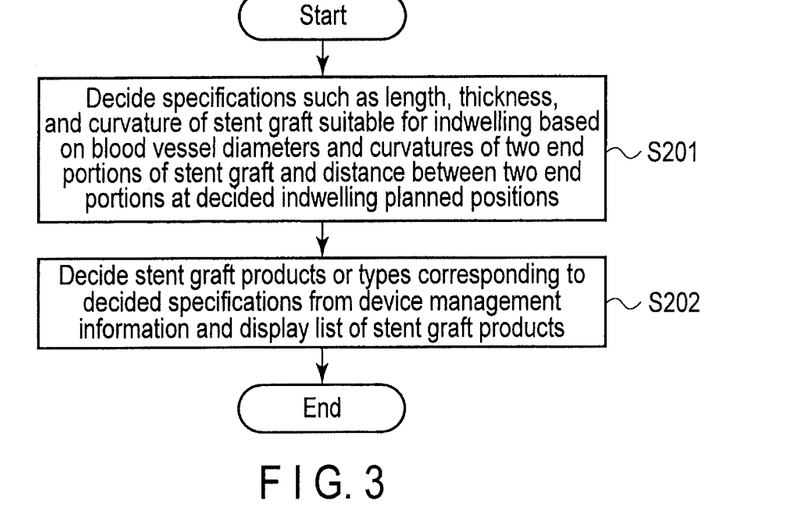
FIG. 3 is a flowchart showing a procedure for stent graft decision support processing by the stent graft indwelling support apparatus in FIG. 1.

FIG. 3 shows stent graft specification decision processing by the stent graft specification decision unit 16. The stent graft specification decision unit 16 decides specifications concerning a stent graft required for the aneurysm treatment based on the stent graft indwelling planned positions and the blood vessel form indices (step S201). The decided specifications include an aneurysm size, neck diameters, and maximum curvature. The stent graft specification decision unit 16 decides an "aneurysm size" from the distance between the indwelling planned positions on the two sides or the diameter of the aneurysm region specified by pattern recognition. The stent graft specification decision unit 16 decides "neck diameters" from blood vessel diameters, average diameters, or maximum diameters at the indwelling planned positions on the two ends of the stent graft. The stent graft specification decision unit 16 decides the maximum value of blood vessel curvatures between the indwelling planned positions of the stent graft as a "maximum curvature".

The stent graft specification decision unit 16 searches an information database concerning many stent graft products stored in advance in the device management information storage unit 15 based on the decided stent graft specifications. This decides at least one stent graft product satisfying the decided stent graft specifications. The display unit 19 displays a list of decided stent graft products (step S202). For example, the display unit 19 displays maker names, corresponding aneurysm sizes, neck diameters, and maximum curvatures as stent graft product information.

Figure 15:
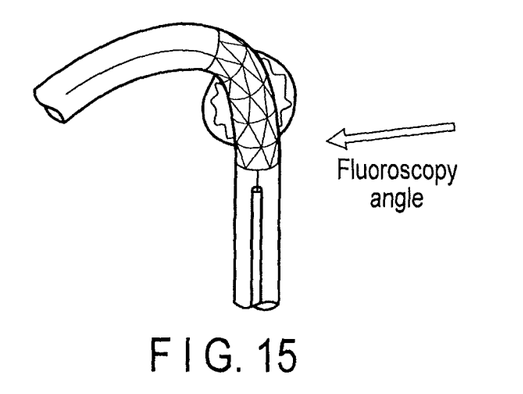
FIG. 15 is a view showing the imaging angle optimal for a visual check of endoleak in step S302 in FIG. 4.

It is necessary to perform follow-up observation after the completion of stent graft indwelling. It is most important in this follow-up observation to check the occurrence of endoleak. The endoleak imaging angle decision unit 17 decides an imaging angle exemplified in FIG. 15 which is most suitable for a check on the occurrence of endoleak. The endoleak imaging angle decision unit 17 may execute this decision, together with indwelling support, at the stage of indwelling support before stent graft indwelling or may execute the decision before a check on the occurrence of endoleak. The latter will be described below.

According to the above description, recommended regions and unrecommended regions are two-dimensional ranges. However, they may be one-dimensional ranges which can be expressed by points and lines or three-dimensional ranges which can be expressed stereoscopically. When expressing recommended regions and unrecommended regions as three-dimensional ranges, this apparatus stereoscopically displays the recommended regions and the unrecommended regions together with a three-dimensional CT image by volume rendering processing like that shown in, for example, FIG. 13 or 15. When rotating and displaying a three-dimensional CT image, the apparatus rotates and displays recommended regions and unrecommended regions together with the three-dimensional CT image. This allows to three-dimensionally recognize the recommended regions and unrecommended regions together with the aneurysm and the blood vessel.

Figure 4:
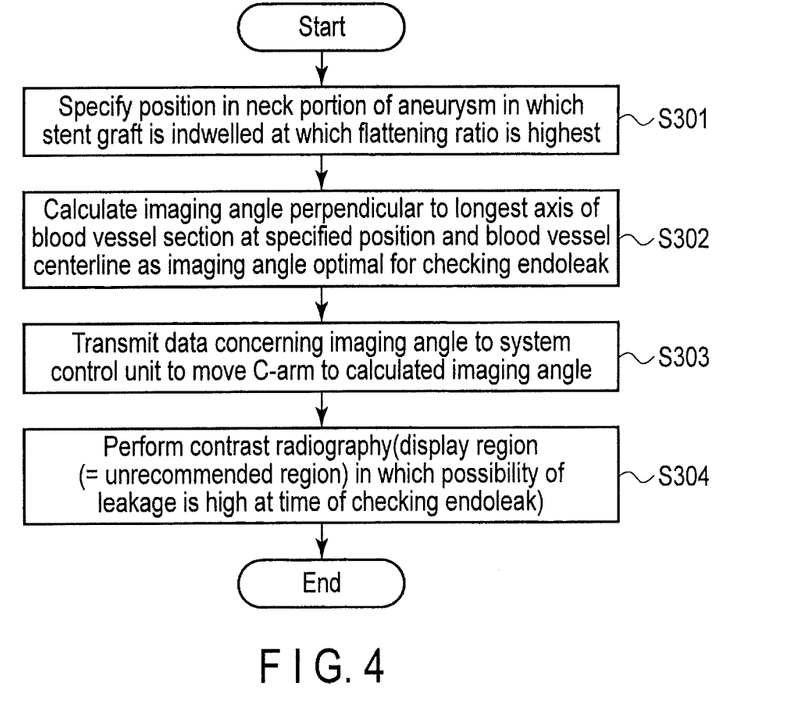
FIG. 4 is a flowchart showing an endoleak check support procedure by the stent graft indwelling support apparatus in FIG. 1.
Figure 13:
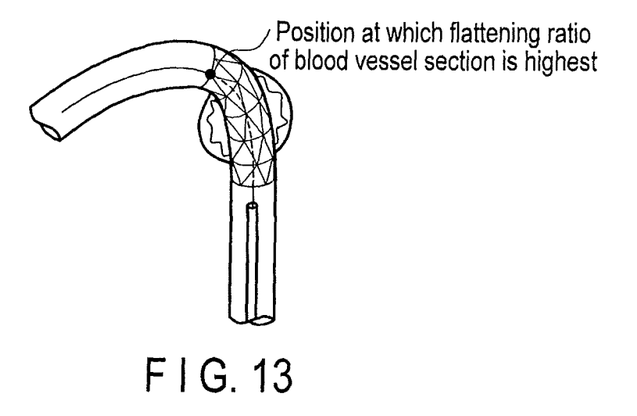
FIG. 13 is a view corresponding to step S301 in FIG. 4.
Figure 14:
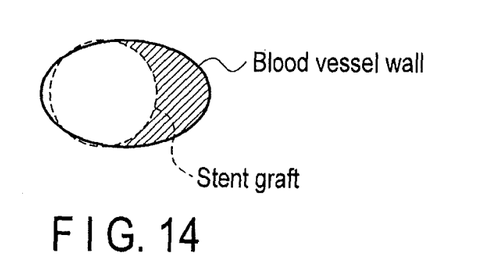
FIG. 14 is a view showing a CT section passing through the position specified in step S301 in FIG. 4.
Figure 16:
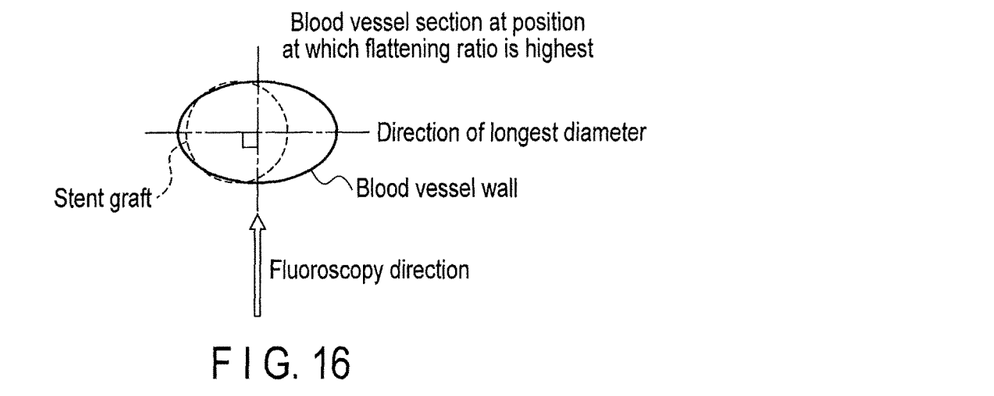
FIG. 16 is a view showing a method of deciding an imaging angle optimal for a visual check of endoleak in step S302 in FIG. 4.
Figure 17:
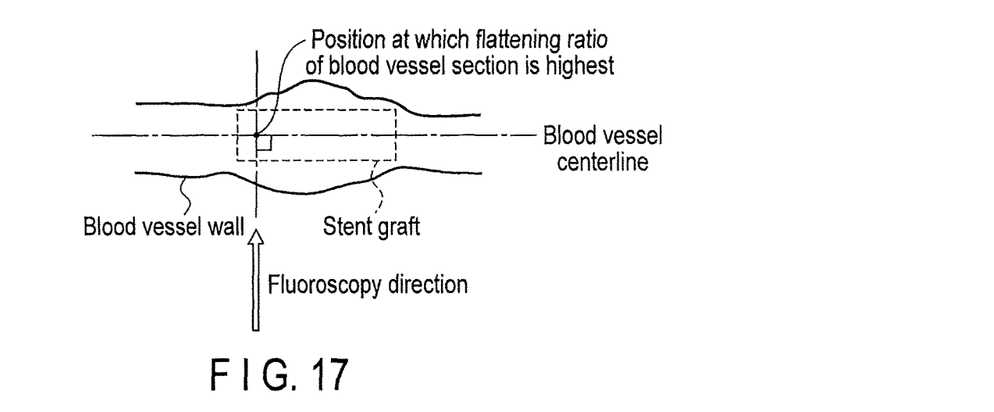
FIG. 17 is a view showing a method of deciding an imaging angle optimal for a visual check of endoleak in step S302 in FIG. 4.

As shown in FIG. 14, the possibility of endoleak is highest at a portion between the stent graft and the blood vessel wall where the gap (hatching) is largest. As shown in FIG. 4, first of all, in step S301, the apparatus specifies, from the latest CT image, a position, in an intra-neck range in which the two ends of the stent graft are in contact with the blood vessel wall, at which the blood vessel flattening ratio is highest, at each stent graft indwelling position (FIG. 13). In step S302, as shown in FIGS. 16 and 17, the apparatus decides, as an imaging angle, a direction orthogonal to a plane determined by the longest diameter passing through the point at which the blood vessel flattening ratio is highest and a blood vessel centerline segment intersecting the point and located near the point.

The apparatus moves the C-arm in accordance with the decided imaging angle under the control of the system control unit 8 (step S303). The apparatus executes contrast radiography at this imaging angle (step S304).

As has been described above, according to this embodiment, it is possible to expect a reduction in endoleak occurrence rate, a reduction in burden on the user, shortening of operation time, a reduction in exposure dose, and a reduction in the amount of contrast medium used.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising:
an image storage memory configured to store data of an image including an aneurysm in an object;
processing circuitry configured to
extract a blood vessel wall region from the image;
specify an aneurysm region based on the extracted blood vessel wall region;
calculate at least one of a blood vessel diameter change rate, a blood vessel curvature, and a blood vessel flattening ratio at each of a plurality of discrete points on the extracted blood vessel wall region other than the aneurysm region;
extract, from the plurality of discrete points, a plurality of unrecommended points at each of which the at least one of the blood vessel diameter change rate, the blood vessel curvature, and the blood vessel flattening ratio exceeds a corresponding one of thresholds;
decide an unrecommended range from a range in which the plurality of unrecommended points constitute a string; and
decide a recommended range for indwelling of a stent graft for the aneurysm by excluding the unrecommended range from the extracted blood vessel wall region; and
a display configured to superimpose and display the recommended range on the stored image.

2. The medical image processing apparatus of claim 1, wherein the recommended range comprises a range displayed two-dimensionally or three-dimensionally.

3. The medical image processing apparatus of claim of 1, wherein the processing circuitry decides the recommended range in accordance with a plurality of discrete points at each of which the blood vessel diameter change rate is less than a threshold corresponding to the blood vessel diameter change rate or another threshold lower than the threshold.

4. The medical image processing apparatus of claim 1, wherein the processing circuitry decides the recommended range in accordance with a plurality of discrete points at each of which the blood vessel curvature is less than a threshold corresponding to the blood vessel curvature or another threshold lower than the threshold.

5. The medical image processing apparatus of claim 1, wherein the processing circuitry decides a blood vessel neck portion which is located outside the unrecommended range and has a length exceeding a necessary length of an end portion of the stent graft as the recommended range.

6. The medical image processing apparatus of claim 1, wherein the decided recommended range is displayed, together with the unrecommended range, while being superimposed on the image.

7. The medical image processing apparatus of claim 1, wherein the display superimposes and displays at least one of the unrecommended range and the recommended range on a live image generated by an external X-ray angiographic diagnostic apparatus.

8. A medical image processing apparatus comprising:
an image storage memory configured to store data of an image including an aneurysm in an object;
processing circuitry configured to
extract a blood vessel wall region from the image;
specify an aneurysm region based on the extracted blood vessel wall region;
calculate at least one of a blood vessel diameter change rate, a blood vessel curvature, and a blood vessel flattening ratio at each of a plurality of discrete points on the extracted blood vessel wall region other than the aneurysm region;
extract, from the plurality of discrete points, unrecommended points at which the at least one of the blood vessel diameter change rate, the blood vessel curvature, and the blood vessel flattening ratio exceeds a corresponding one of thresholds;
decide an unrecommended range which is not recommended for indwelling of a stent graft for the aneurysm in accordance with a point string range of the extracted unrecommended points;
decide a recommended range for indwelling of the stent graft for the aneurysm by excluding the unrecompensed range from the extracted blood vessel wall region; and
a display configured to superimpose and display at least one of the recommended range and the unrecommended range on the stored image.

9. The medical image processing apparatus of claim 8, wherein the processing circuitry sets a local range including the aneurysm in the image as a region of interest, and the processing circuitry localizes a processing range to the region of interest.

10. The medical image processing apparatus of claim 8, wherein the processing circuitry decides the recommended range in which both the blood vessel diameter change rate and the blood vessel curvature each are lower than a corresponding one of the thresholds or another threshold lower than the threshold.

11. The medical image processing apparatus of claim 8, wherein the processing circuitry excludes a plaque portion or a calcified portion identified from the image from the recommended range.

12. The medical image processing apparatus of claim 8, wherein the decided recommended range is displayed, together with the unrecommended range, while being superimposed on the image.

13. The medical image processing apparatus of claim 8, wherein the display superimposes and displays at least one of the unrecommended range and the recommended range on a live image generated by an external X-ray angiographic diagnostic apparatus.

14. The medical age processing apparatus of claim 8, wherein the processing circuitry changes the threshold in accordance with an operator instruction.

15. The medical image processing apparatus of claim 8, wherein the processing circuitry decides specifications concerning a thickness, a curvature, and a length required for the stent graft in accordance with blood vessel diameters of two end portions of the stent graft at indwelling planned positions, a maximum curvature of the two end portions, and a length between the two end portions which are set on the image in accordance with an operator instruction.

16. The medical image processing apparatus of claim 15, wherein the processing circuitry specifies a stent graft product or a stent graft type suitable for the specifications from stent graft production management information.

17. The medical image processing apparatus of claim 8, wherein the processing circuitry specifies a position indicating a maximum blood vessel flattening ratio at two end portions of the stent graft Which are located at indwelling planned positions so as to superimpose and display the position as a position on the image at which a possibility of occurrence of endoleak is high.

18. The medical image processing apparatus of claim 17, wherein the processing circuitry decides an imaging angle orthogonal to a blood vessel long axis at a position indicating the maximum blood vessel flattening ratio and a blood vessel centerline.

19. A medical image processing method comprising:

extracting a blood vessel wall region from an image including an aneurysm in an object;

specifying an aneurysm region based on the extracted blood vessel wall region;

calculating at least one of a blood vessel diameter change rate, a blood vessel curvature, and a blood vessel flattening ratio at each of a plurality of discrete points on the extracted blood vessel wall region other than the aneurysm region;

extracting, from the plurality of discrete points, unrecommended points at which the at least one of the blood vessel diameter change rate, the blood vessel curvature, and the blood vessel flattening ratio exceeds a corresponding one of thresholds;

deciding an unrecommended range which is not recommended for indwelling of a stent graft for the aneurysm in accordance with a point string range of the extracted unrecommended points;

deciding a recommended range for indwelling of the stent graft for the aneurysm by excluding the unrecommended range from the extracted blood vessel wall region; and superimposing and displaying at least one of the recommended range and the unrecommended range on the stored image.

20. The medical image processing method of claim 19, wherein the recommended range in which both the blood vessel diameter change rate and the blood vessel curvature each are lower than a corresponding one of the thresholds or another threshold lower than the threshold is decided.

21. The medical image processing method of claim 20, wherein the decided recommended range is displayed, together with the unrecommended range, while being superimposed on the image.

* * * * *